United States Patent
Brown et al.

(10) Patent No.: US 6,714,627 B1
(45) Date of Patent: Mar. 30, 2004

(54) COLLIMATOR FOR RADIOTHERAPY APPARATUS

(75) Inventors: Kevin John Brown, Horsham (GB); Peter Williams, Withington (GB); John Wong, Royal Oak, MI (US); Di Yan, Royal Oak, MI (US)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/786,065

(22) PCT Filed: Jul. 19, 1999

(86) PCT No.: PCT/GB99/02324

§ 371 (c)(1),
(2), (4) Date: May 24, 2001

(87) PCT Pub. No.: WO00/13189

PCT Pub. Date: Mar. 9, 2000

(30) Foreign Application Priority Data

Aug. 28, 1998 (GB) .............................. 9818704

(51) Int. Cl.$^7$ ................................................ G21K 1/04
(52) U.S. Cl. .......................................... 378/152; 378/65
(58) Field of Search ................................ 378/147, 148, 378/149, 150, 151, 152, 155, 156, 145

(56) References Cited

U.S. PATENT DOCUMENTS 4,868,843 A * 9/1989 Nunan ........................ 378/152
6,266,393 B1 * 7/2001 Ein-Gal ...................... 378/152
6,388,816 B2 * 5/2002 Brown et al. ............... 359/641

FOREIGN PATENT DOCUMENTS

| EP | 0 314 214 A | 5/1989 |
| EP | 0 685 200 A | 12/1995 |
| EP | 0 751 532 A | 1/1997 |

* cited by examiner

*Primary Examiner*—Louis Arana
(74) *Attorney, Agent, or Firm*—Kinney & Lange, P.A.

(57) ABSTRACT

A radiotherapy apparatus comprises a first collimator and a second collimator, the first collimator being a multi-leaf collimator, the second collimator comprising a plurality of slits having a width which is a fraction of the width of the leaves of the first collimator, the first and second collimators being aligned such that each slit of the second collimator is associated with a leaf of the first collimator. A first irradiation is made, during which the first collimator will define the outer edge of the irradiation pattern, and the second collimator will serve to narrow the effective width of each leaf of the first collimator. This narrowing is a simple function of the relative widths of the slits of the second collimator and the leaves of the first. This will leave gaps in between the slits of the second collimator, which can then be filled by moving one or more of the patient, first and second collimators, so as to irradiate an area omitted in the first irradiation. In this second irradiation, the positions of the leaves of the first collimator are adjusted as necessary. This process is then repeated until the entire target area has been irradiated. Suitable values for the fraction are ½, 1/3, 1/4, or ⅕.

20 Claims, 7 Drawing Sheets

COLLIMATOR FOR RADIOTHERAPY APPARATUS

FIELD OF THE INVENTION

The present invention relates to a collimator for use in radiotherapy.

BACKGROUND ART

Radiotherapy is routinely employed for the treatment of invasive medical conditions such as cancer. The essential principle of radiotherapy is that the applied beam is apt to kill cells in its path. Thus, if the beam is directed at a cancerous or otherwise abnormal area the cells would eventually destroyed. However, it is inevitable that damage will also be caused to surrounding healthy tissue, and if this is not appropriately limited then the side effects for the patient could well be severe.

Figure 1:
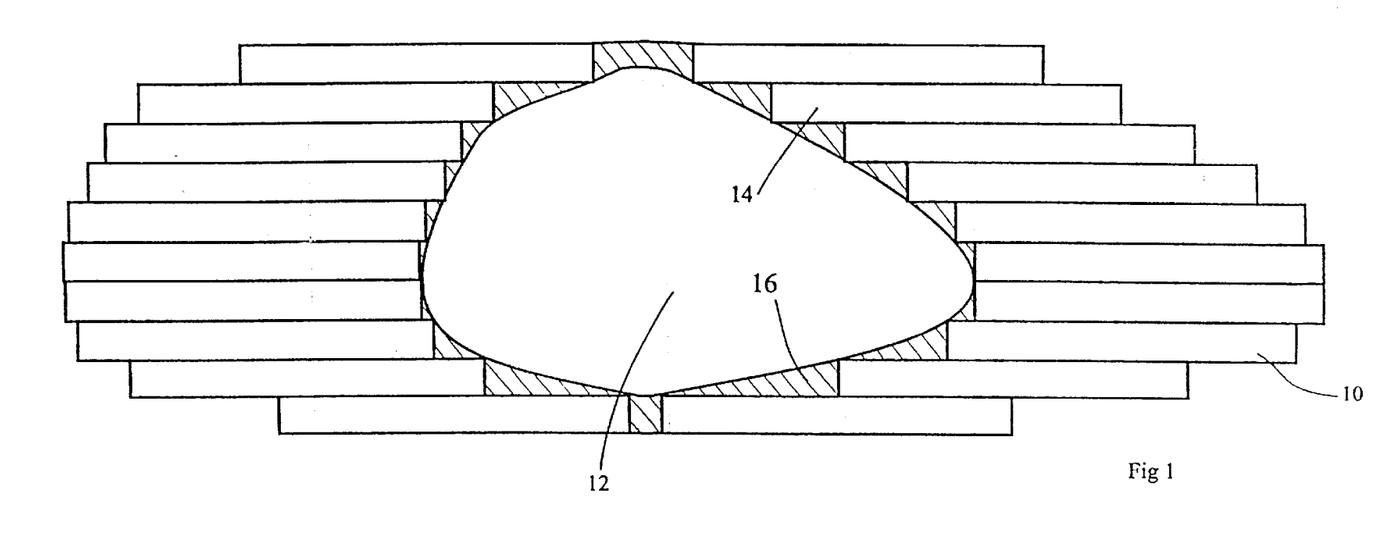
FIG. 1 illustrates a conventional multi-leaf collimator, and has been described already.

Such limitation is commonly achieved by collimating the beam so as to extend only over the minimum necessary area, to include all of the cancer but only a minimum amount of healthy surrounding tissue. Multi-leaf collimators are well known for this purpose, and comprise two banks of individually extendable leaves which can be extended into and out of the radiation beam so as to shape the emergent beam at will. FIG. 1 shows the effect of a multi-leaf collimator. The leaves 10 are extended into the beam and prevent radiation reaching the patient in those areas. Each leaf 10 is typically stopped just short of the area 12 to be irradiated. Thus, the areas beneath the leaves (such as at 14) are not irradiated, limiting side effects of the treatment.

FIG. 1 also illustrates the inherent limitation of multi-leaf collimators, which is that areas 16 are unnecessarily irradiated due to the finite width of the leaves 10. Efforts have therefore been directed in producing multi-leaf collimators with narrower leaves, to achieve higher spatial resolution and limit the size of the unnecessarily irradiated area 16. However, this presents significant engineering difficulties since the leaves must be relatively deep in order to present a high opacity to x-rays. In addition, there must be no gaps between the leaves through which radiation could leak. Thus, the engineering difficulties in accurately moving close fitting narrow heavy leaves are significant. Nevertheless, so-called "micro-multi-leaf collimators" have been developed. These typically have a very limited field size in order to alleviate the engineering difficulties.

SUMMARY OF THE INVENTION

The present invention seeks to provide a collimator in which the irradiation pattern of such a micro multi-leaf collimator can be achieved without the associated engineering difficulties and limited field size.

It therefore provides a radiotherapy apparatus comprising a first collimator and a second collimator, the first collimator comprising a plurality of elongate leaves lying alongside each other, each being moveable longitudinally, the second collimator comprising a plurality of slits, the first and second collimators being aligned such that each slit of the second collimator is associated with at least one leaf of the first collimator, the slits having a width which corresponds to a fraction of the width of the leaves.

The slit widths correspond to the leaf widths in that the projected image of the slits on the patient is a fraction of the projected image of the leaves on the patient. Where the first and second collimators are immediately adjacent, this will mean that the physical width of the slits is a fraction of the physical width of the leaves. Where the two collimators are at different locations along the beam, an appropriate scaling will be necessary such that the projected dimensions at the patient are an appropriate fraction.

It is preferred if the first collimator is above the second, but this is not in fact necessary and the second collimator can well be above the first.

It is also preferred that the slits are focused on the radiation source.

According to the invention, a first irradiation is made, during which the first collimator will define the outer edge of the irradiation pattern, and the second collimator will serve to narrow the effective width of each leaf of the first collimator. This narrowing is a simple function of the relative widths of the slits of the second collimator and the leaves of the first. This will leave gaps in between the slits of the second collimator, which can then be filled by moving one or more of the patient, first and second collimators, so as to irradiate an area omitted in the first irradiation. In this second irradiation, the positions of the leaves of the first collimator are adjusted as necessary. This process is then repeated until the entire target area has been irradiated.

Thus, by use of the collimator the present invention allows the resolution of a micro multi-leaf collimator to be provided with no associated engineering difficulties, the only cost being the need for repeat irradiations. The treatment time for each irradiation could be reduced by selecting higher dose rates.

One way of providing the repeat irradiations is to make the second collimator movable relative to the first. However, it is preferable for the first and second collimators to be movable together relative to the patient. This could obviously be achieved either by moving the collimators en bloc, or by fixing the first and second collimators and moving the patient. Alternatively, the patient could be moved continuously relative to the source, the first collimator leaves being adjusted as necessary as the treatment progresses.

The second collimator is preferably removable from the apparatus, thereby to enable exchange with alternative second collimators. These alternative second collimators could have a different fractional width, or a different irradiatable area.

Suitable values for the fraction are $\frac{1}{2}$, $\frac{1}{3}$, $\frac{1}{4}$ or $\frac{1}{5}$.

In general, narrow slits will result in a greater number of repeat irradiations. This means that the opacity to X-rays of the second collimator must be correspondingly greater, which implies a more massive device.

Wider slits will, in general, reduce the treatment times, but will not achieve as good conformation to the desired irradiation area. It will therefore be advantageous to choose the widest slits commensurate with the desired accuracy.

The present invention therefore also relates to a kit of parts comprising the apparatus as defined above in combination with alternative second collimators exhibiting different fractional widths.

BRIEF DESCRIPTION OF DRAWINGS

Embodiments of the present invention will now be described by way of example, with reference to the accompanying Figures in which.

DETAILED DESCRIPTION OF THE INVENTION

FIG. 1 has been described already, and therefore no further description will be given herein.

Figure 2:
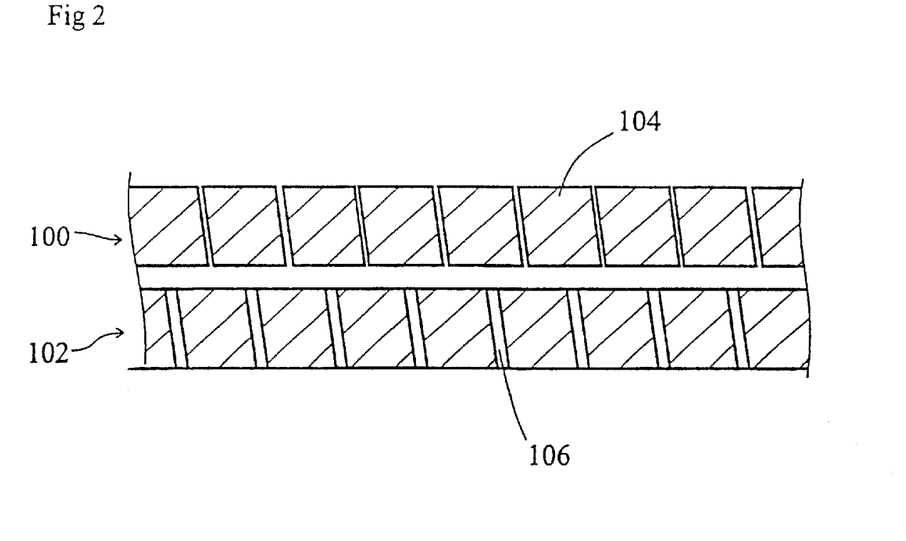
FIG. 2 is a vertical section through a collimator according to the present invention.
Figure 3:
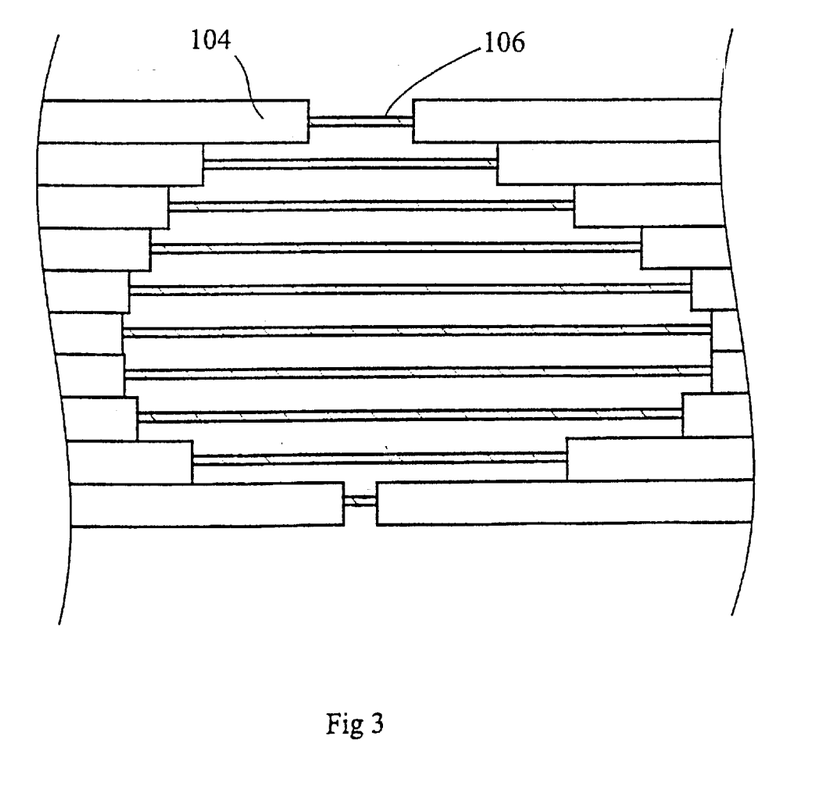
FIG. 3 is a top view of FIG. 1.

FIGS. 2 and 3 illustrate the first embodiment of the present invention. According to this embodiment, a first collimator 100 is suspended above a second collimator 102. The first collimator 100 is constructed as a standard multi-leaf collimator comprising a plurality of leaves 104 alongside each other and which are slidable longitudinally relative to one another. FIG. 2 shows the view along the length of the leaves. Thus, the leaves appear head-on.

The second collimator 102 is below the first and is a solid mass except for slits 106. These slits 106 are positioned immediately below the centre lines of leaves 104 of the first collimator 100, although this position may be moveable as described later.

Referring to FIG. 3, the combination of the first and second collimators 100, 102 means that the view along the x-ray beam shown in FIG. 3 is essentially that of the slits 106 delimited in length by the leaves 104 of the first collimator 100.

Figure 4:
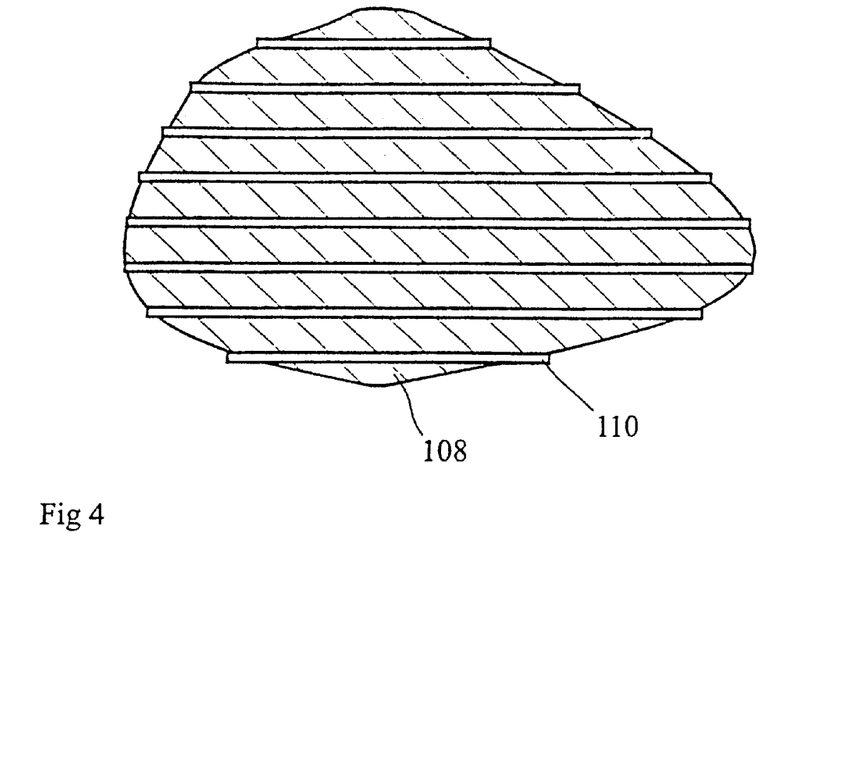
FIG. 4 illustrates the effect achieved by the present invention after the first irradiation.

FIG. 4 shows the effect of this collimation arrangement. An area 108 is to be irradiated, shown shaded. The first irradiation, as delivered by the collimator positions shown in FIG. 3, will produce a series of stripes 110 across the area 108. These correspond to the exposed areas of the slits 106.

It is then necessary either to move the patient beneath the collimator by a distance equal to the projected width of the slits 106, or to move the first and second collimators over the patient by an equal distance, or to move the second collimator 102 relative to the first collimator 100 by that distance. All three arrangements will then allow a further irradiation to be made in which the stripes 110' are effectively adjacent the stripes 110 of the first irradiation. The leaf positions of the first collimator 100 can be adjusted between each irradiation as required. The projected stripe will almost always include a penumbra and reference herein to stripe width, adjacent stripes etc should be interpreted taking this into account. For example, it is known to adjust the spacing of neighbouring stripes so as to match the intensity profile and achieve a near uniform delivered intensity.

Figure 5:
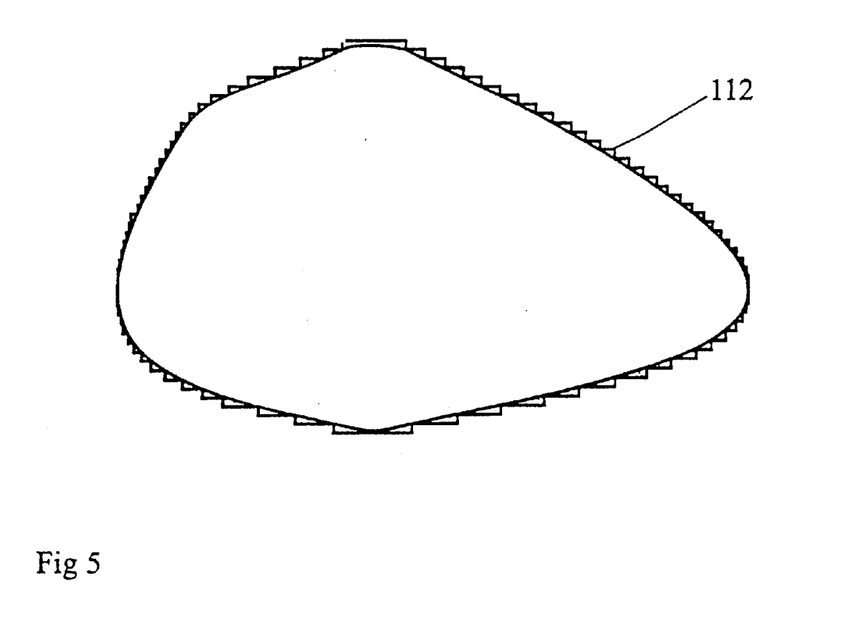
FIG. 5 shows the effect achieved by the present invention after completion of irradiation.

After several such irradiations have been completed, the total number required being determined by the relative widths of the leaves 104 of the first collimator as opposed to the slits 106 of the second collimator, the complete area 108 will have been irradiated. The net effect of the multiple irradiations will be as shown in FIG. 5, in which it can be seen that the excess irradiated area 112 is significantly smaller than the area 16 of FIG. 1. However, this pseudo-micro-multi-leaf collimator effect has been achieved using only a standard size multi-leaf collimator in combination with a simple (and hence inexpensive) secondary collimator.

It was mentioned above that either the patient, both collimators, or only the second collimator could be moved between irradiations. It is preferred to move both collimators together, for reasons which will be explained.

If the patient alone is moved, this will normally be in a transverse direction relative to the leaves 104 and slits 106. However, there will inevitably be some divergence of the beam during its passage between the collimator and the patient, and the result of this will be that areas within the patient which are distant from the source will be irradiated twice by the divergent portions of adjacent beams, whilst areas on the patient closest to the source are likely to be under-irradiated.

As the motion is very small, typically 2–3 mm, this effect is negligible with this device, unlike other applications of radiotherapy where the motion is 20–100 mm and this 'matchline' is an undesirable effect.

Another possibility is to move the patient in a continuous motion simultaneously moving the leaves to correspond. This motion will be very slow, typically 1 mm in 30 seconds and therefore imperceptible to the patient. This technique averages any inaccuracies in matching the fields over a larger area, thus reducing the maximum variation.

Figure 6:
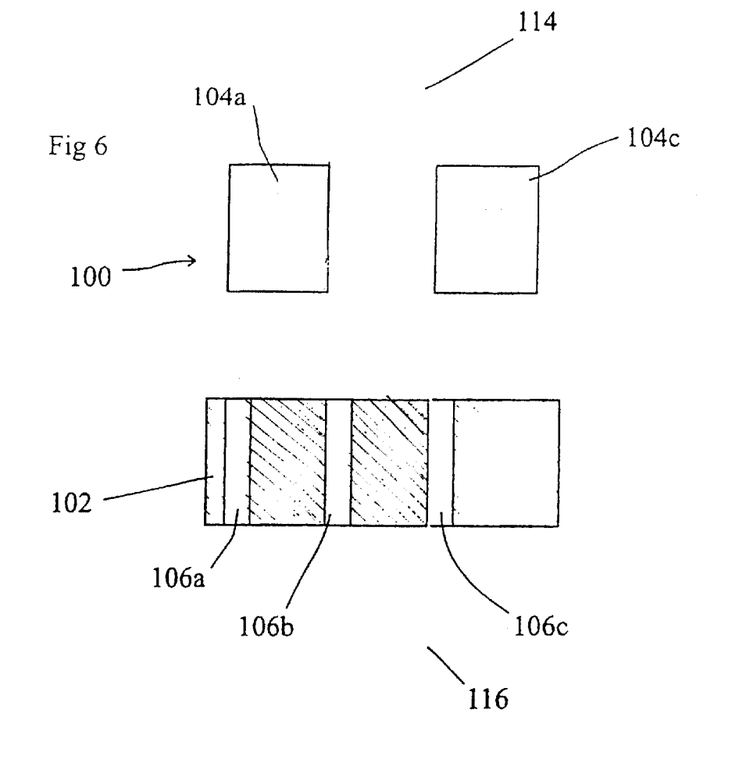
FIG. 6 shows a first means of adjusting the collimator position relative to the patient.

FIG. 6 illustrates the potential difficulty in moving the second collimator 102 relative to the first 100. This arises from the fact that the irradiation source is inevitably non-point like. In FIG. 6, collimator leaves 104A and 104C of the first collimator 100 are extended but leaf 104B lying immediately between is withdrawn. Thus, the intention is to project a stripe 106 only at the position corresponding to leaf 104B (not visible).

The second collimator 102 has corresponding slits 106A, 106B and 106C. Slits 106A and 106C-are not intended to be irradiated since they are beneath extended leaves 104A and 104C. Slit 106B should be irradiated since it is beneath withdrawn leaf 104B.

In the position shown, the second collimator 102 is at the limit of its travel relative to the first collimator 100, with the left hand (as shown) edge of the slits 106A being directly beneath the left hand edge of the leaves 104. As shown, the x-ray beam 114 passes between leaves 104A and 104C of the first collimator 100 and correctly passes through slit 106B of the second collimator. However, the necessary engineering tolerances and the slight transparency of all materials to x-rays means that there is a small leakage path on one side along the edge of leaf 104C and through slit 106C. This gives rise to a "ghost" irradiation in areas which were not intended to be irradiated. Whilst it may be possible to minimise this ghosting in particular arrangements, this means that this method of relative movement is not preferred.

Figure 7:
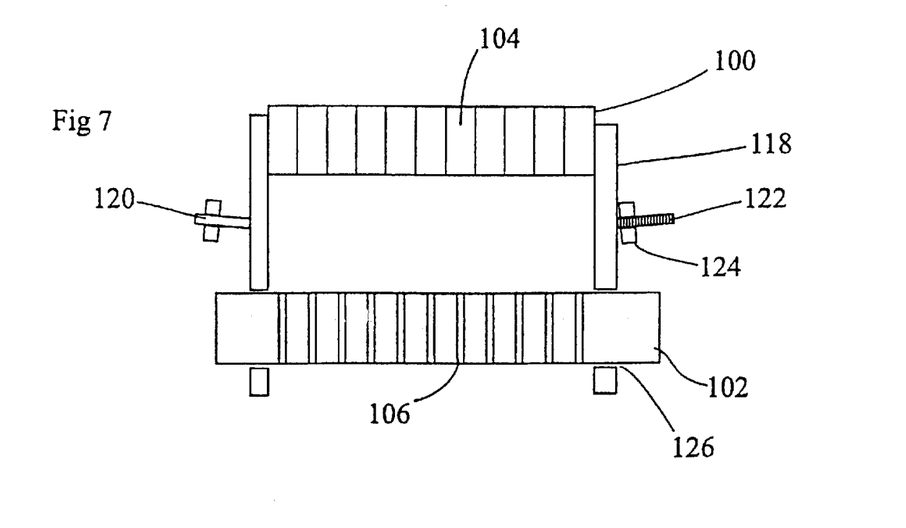
FIG. 7 illustrates a second means of adjusting the collimator positions relative to the patient.

FIG. 7 illustrates the preferred method of achieving relative motion. The first collimator 100 and the second collimator 102 are both supported on a frame 118 in an essentially fixed arrangement. In this arrangement, the slits 106 of the second collimator 102 are preferably directly beneath the leaves 104 of the first collimator 100. It is possible to offset the slits 106 slightly without affecting performance, but an excessive offset would of course introduce the difficulties with respect to FIG. 6. The entire support 118 is in turn supported on a set of bearings 120 on one side and a threaded drive screw 122 on the other side.

The drive screw 122 is held in a rotatable nut 124. Thus, rotation of the nut 124 will cause the support 118 to slide within the bearing 120, adjusting the positions of both collimators simultaneously.

As shown in FIG. 7, the bearing 120 and drive screw 122 are tilted slightly so as to cause the support 118 to move along a circumferential path, centred on the radiation source. This means that beam divergence effects mentioned above are minimised.

FIG. 7 also shown the second collimator 106 to be received within an aperture 126. This allows the second collimator 102 to be removed as necessary and replaced with alternative collimators. A suitable indexing means will of course need to be provided to locate the respective second collimator 102 in the correct position, but this should not present difficulties. The advantage of providing interchangeable second collimators 102 is that alternatives could be provided in which the width ratios as between the first and second collimators differ, or in which the spacial extent of the slits 106 on the second collimator differs. This means that the accuracy of the collimation can be selected according to the dose to be applied and the time available, and that small-area high precision second collimators can be provided for precision work together with alternative large-area lower precision devices for standard work.

Figure 8:
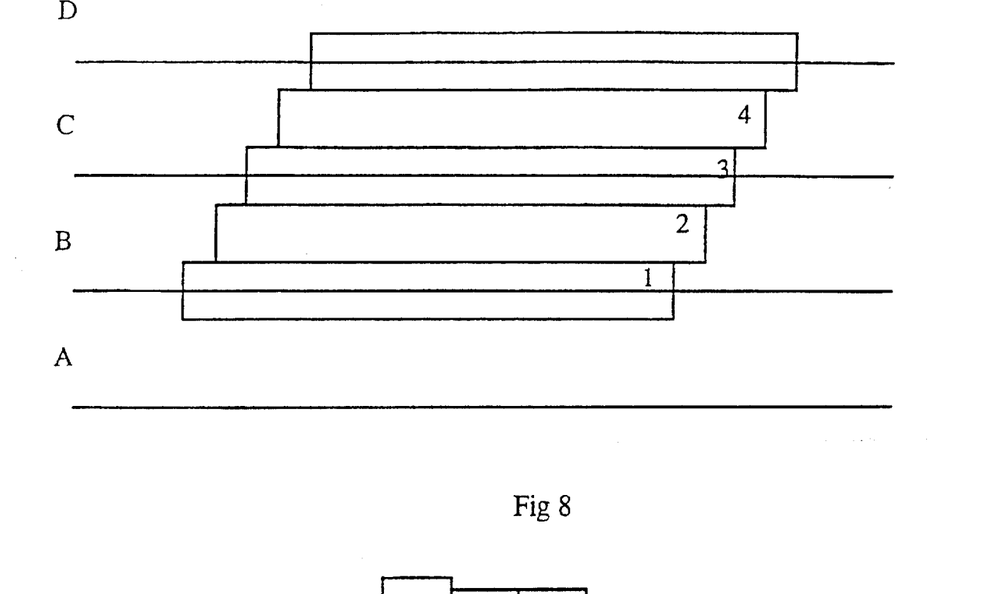
FIG. 8 illustrates an alternative construction.

FIG. 8 shows an alternative arrangement in which the potential difficulty illustrated in FIG. 6 is eliminated. As shown, the slits of the second collimator are placed at a 20 mm pitch with a 5 mm width. The first collimator has leaves A, B, C & D of a 10 mm width. According to this arrangement, the second collimator is moved relative to the first collimator such that the slit straddles leaves A and B. This is shown as position 1. A first irradiation than takes place in which the width of the radiation stripe is controlled by both leaves acting together. Normally, this would involve them being placed at the same point. The second collimator is then moved by 5 mm to position 2 in which it lies completely beneath leaf B. A second irradiation takes place, delimited by leaf B only. The second collimator then moves by a further 5 mm to position 3 and a third irradiation takes place, delimited this time by leaves B and C. Finally, the second collimator moves by a still further 5 mm to position 4 and a final fourth irradiation take place delimited by leaf C only.

In this manner, each slit is alternately delimited by a single leaf and a pair of leaves.

It will be apparent that during the fourth irradiation, leaf A covers the next adjacent slit and therefore delimits the adjacent radiation stripe.

At no time during this process are the edges of any leaves and slits aligned during an irradiation. Therefore, the potential difficulty illustrated in FIG. 6 is avoided completely, the only cost being further irradiations. In this example, a doubling of the resolution is achieved through a mere quadrupling of the number of irradiations.

Figure 9A:
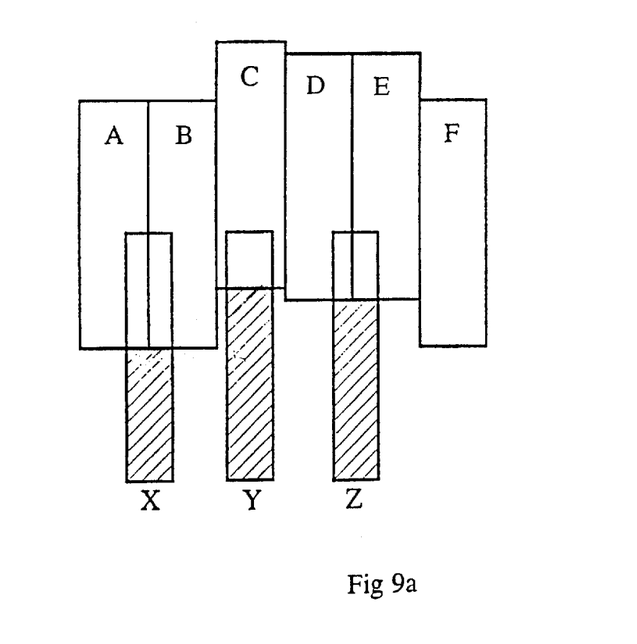
FIGS. 9a to 9c illustrate a further alternative construction.
Figure 9B:
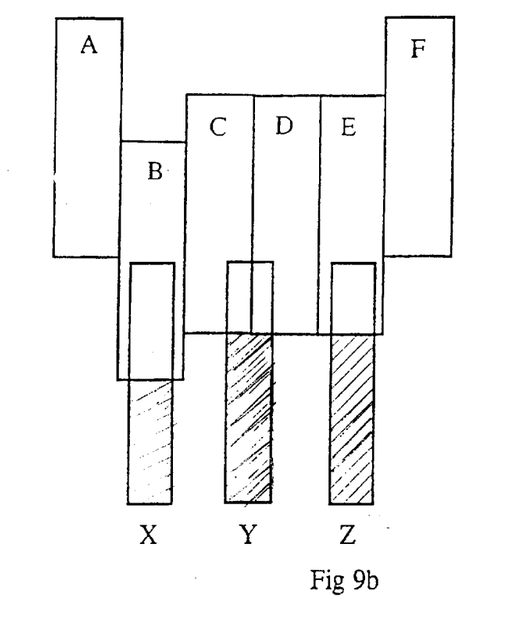
Figure 9C:
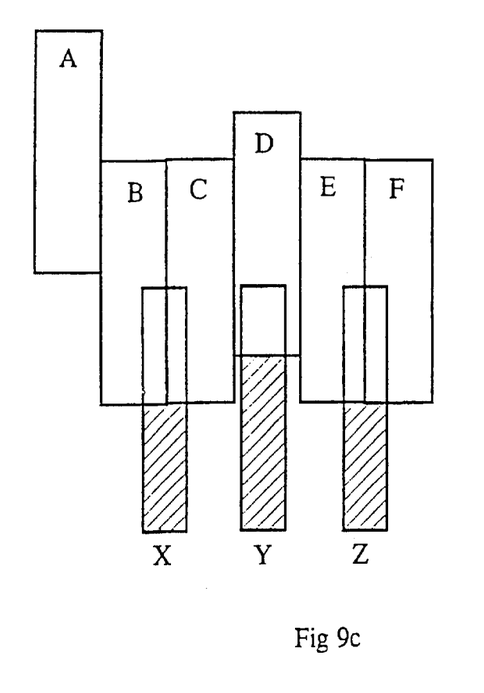

FIGS. 9a to 9c illustrate a further alternative in which the same doubling of resolution is achieved without any "excess" irradiation but though only three irradiations. In this further alternative, the leaves A, B, C, D, E & F of the first collimator are at a 10 mm pitch and the slits X, Y & Z in the second collimator are 5 mm wide and at a 15 mm pitch.

FIG. 9a illustrates the first irradiation. Slit X is delimited by leaves A and B, positioned over the join between them. Slit Y is therefore directly over leaf C, as its pitch is equivalent to 1½ leaves. Sit Y is therefore delimited by leaf C alone. Slit Z lies over leaves D and E.

For the second irradiation, the second collimator is moved by 5 mm so as to irradiate the adjacent stripe. Slit X therefore lies over and is delimited by leaf B only. Slit Y is delimited by leaves C and D, and slit Z is delimited by leaf E.

Finally, prior to a third irradiation, the second collimator is moved by a further 5 mm. Slit X will then lie over and be delimited by leaves B and C. Slit Y is delimited by leaf D and slit Z is delimited by leaves E and F.

Thus, by simultaneously delimiting by single leaves and adjacent leaf pair, greater efficiency is achieved and the number of irradiations required is reduced. This will in turn reduce the treatment time necessary.

Figure 10:
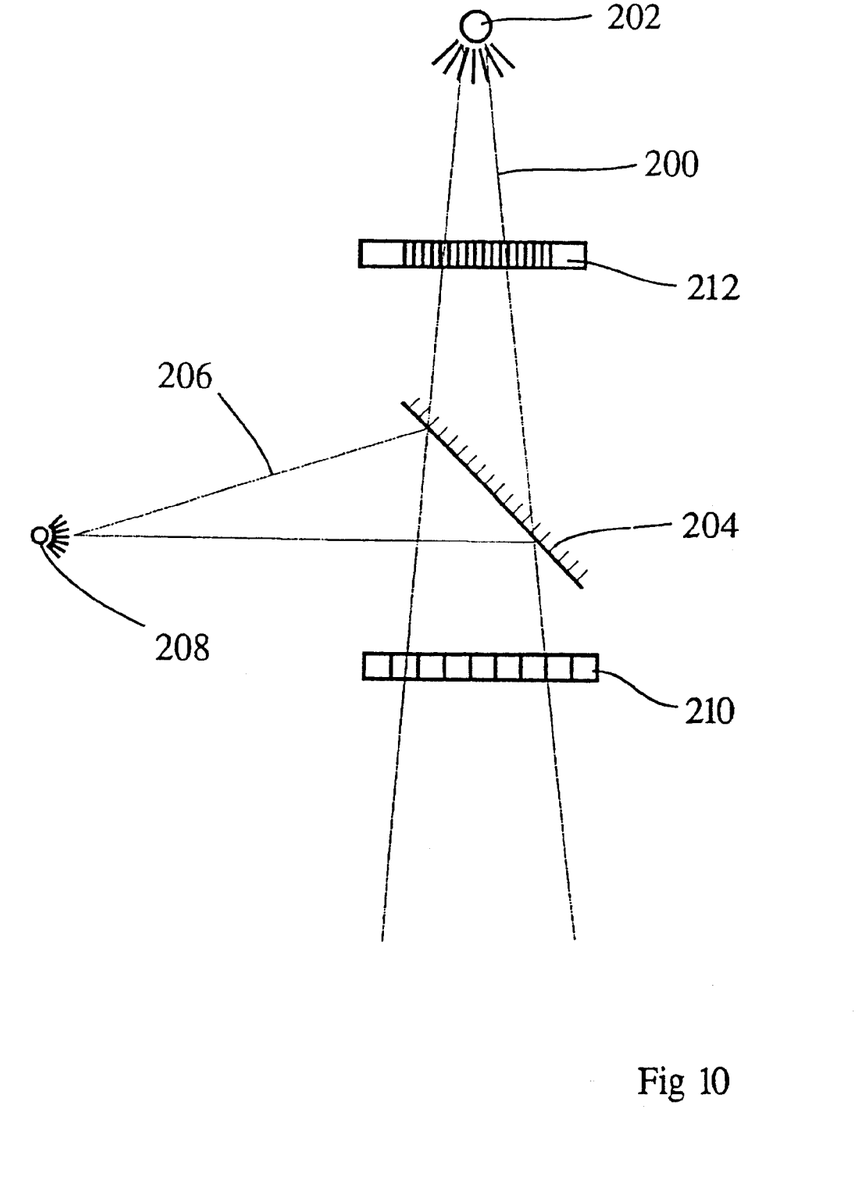
FIG. 10 illustrates an advantageous order for the collimators along the beam path.

FIG. 10 illustrates schematically a preferred linear arrangement of the structure of the invention along the path of the radiation beam. A beam of radiation 200 is emitted by a source 202. It is conventional for there to be a light reflecting mirror 204 in the path of the beam 200, angled at approximately 45° to the radiation beam axis, in order to reflect a light beam 206 from a light source 208 onto the path of the radiation beam 200. Of course, the mirror 204 can be at other angles, and the location of the light source 206 adjusted accordingly. Thus, the therapist can position the patient beneath the apparatus with the radiation beam 200 off (ie shielded) and the light beam 206 on. This will then cast a light on the patient illuminating the area to be treated. This enables the therapist to confirm that the patient is correctly located. During irradiation, the mirror 204 is effectively transparent to X-rays and the like and therefore has substantially no effect on the treatment.

As shown in FIG. 10, the first collimator 210 is below the mirror 204 and therefore modulates the light beam for the purpose of positioning the patient. This modulation will be to the lower resolution of the first collimator as compared to the apparatus as a whole, but for positioning purposes this will not matter. The second collimator 212 is above the mirror 204 and therefore does not affect the light beam 206. As a result, positioning can be carried out using a full light source as opposed to a series of narrow stripes.

Locating the second collimator 212 above the mirror 204 also means that the beam size to be collimated is substantially narrower. The second collimator can therefore be correspondingly smaller, reducing its weight and associated material cost. It will also be within the interior of the apparatus, rendering it easier to displace by small distances for successive irradiations. It is preferred that the second collimator can be removed from the radiation beam 200, eg by sliding to one side, in order to allow conventional use of the apparatus of use with other collimators.

It will be appreciated that many variations can be made to the above-described embodiments without departing from the scope of the present invention. Such variations are of course intended to fall within the scope of this Application.

This device can of course be used in place of existing multi-leaf collimators, in similar treatment patterns. This could include (for example) intensity modulated radiotherapy methods.

What is claimed is:

1. Radiotherapy apparatus comprising a first collimator and a second collimator, the first collimator comprising a plurality of elongate leaves lying alongside each other, each being moveable longitudinally, the second collimator comprising a plurality of slits, the first and second collimators being aligned such that each leaf of the first collimator at least partially covers a slit of the second collimator, the slits having a width which corresponds to a fraction of the width of the leaves.

2. Radiotherapy apparatus according to claim 1 wherein the first collimator is above the second.

3. Radiotherapy apparatus according to claim 1, wherein the slits are focused on the source of radiation within the apparatus.

4. Radiotherapy apparatus according to claim 1, in which the second collimator is movable relative to the first.

5. Radiotherapy apparatus according to claim 1, in which the first and second collimators are movable together relative to the patient.

6. Radiotherapy apparatus according to claim 1, adapted to allow a patient to be moved continuously relative to the source, the first collimator leaves being adjustable as the treatment progresses.

7. Radiotherapy apparatus according to claim 1, in which the fraction is one of ½, 1/3, 1/4 or 1/5.

8. Radiotherapy apparatus according to claim 1, in which the second collimator is removable from the apparatus, thereby the enable exchange with an alternative second collimator.

9. Radiotherapy apparatus according to claim 8 in which the alternative second collimator has a different fractional width.

10. Radiotherapy apparatus according to claim 8, in which the alternative second collimator has a different irradiatable area.

11. Radiotherapy apparatus according to claim 1, in which the second collimator is above the first.

12. Radiotherapy apparatus according to claim 1, in which the second collimator is above a light reflecting mirror.

13. Radiotherapy apparatus according to claim 1, in which the first collimator is below a light reflecting mirror.

14. Radiotherapy apparatus according to claim 1, in which the second collimator is positionable such that during an irradiation at least one slit is aligned with a pair of leaves in the first collimator.

15. Radiotherapy apparatus according to claim 14 in which the centreline of the slit is aligned with the adjacent edges of the pair of leaves.

16. Radiotherapy apparatus according to claim 1, in which the pitch of the slits in the second collimator is approximately an integer multiple of the width of the leaves in the first collimator.

17. Radiotherapy apparatus according to claim 1, in which the pitch of the slits in the second collimator is approximately an integer multiple of the width of the leaves in the first collimator plus one half that width.

18. A kit of parts comprising the apparatus as defined above in claim 1, in combination with alternative second collimators exhibiting different fractional widths.

19. A method for performing radiotherapy comprising:

aligning leaves of a first collimator with slits of a second collimator to produce at least one substantially planar beam of radiation;

sweeping the at least one substantially planar beam of radiation through the first and the second collimators and across a selected area of a patient lying in a plane transverse to that of the beam; and modulating a width of the at least one substantially planar beam to map out an irradiated area on the patient.

20. The method of claim 19 wherein the slits of the second collimator either allow completely or block entirely a portion of the at least one substantially planar beam.

* * * * *

UNITED STATES PATENT AND TRADEMARK OFFICE
CERTIFICATE OF CORRECTION

PATENT NO. : 6,714,627 B1
DATED : March 30, 2004
INVENTOR(S) : Kevin John Brown et al.

It is certified that error appears in the above-identified patent and that said Letters Patent is hereby corrected as shown below:

<u>Column 5,</u>
Line 66, delete "11/2 leaves. Sit", insert -- 1 ½ leaves. Slit --

Signed and Sealed this

Twenty-fifth Day of January, 2005

JON W. DUDAS
*Director of the United States Patent and Trademark Office*